US00PP25722P3

(12) United States Plant Patent
Egger

(10) Patent No.: US PP25,722 P3
(45) Date of Patent: Jul. 14, 2015

(54) ***X HEUCHERELLA* PLANT NAMED 'COPPER CASCADE'**

(50) Latin Name: ***X Heucherella* hybrid**
Varietal Denomination: Copper Cascade

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 186 days.

(21) Appl. No.: 13/987,660

(22) Filed: Aug. 20, 2013

(65) Prior Publication Data

US 2015/0059034 P1 Feb. 26, 2015

(51) Int. Cl.
*A01H 5/12* (2006.01)

(52) U.S. Cl.
USPC ..... Plt./441

(58) Field of Classification Search
None
See application file for complete search history.

*Primary Examiner* — June Hwu
(74) *Attorney, Agent, or Firm* — Klarquist Sparkman, LLP

(57) ABSTRACT

A new and distinct *X Heucherella* plant substantially as shown and described, characterized by red colored leaves with a pinkish veil and dark pattern along veins, a low dense trailing habit with good branching, medium size, ovate to orbicular leaves with shallow palmate lobing, and excellent vigor.

1 Drawing Sheet

Botanical denomination: *X Heucherella* hybrid.

Variety designation: 'Copper Cascade'.

Cross reference to sibling: *X Heucherella* 'Gold Cascade' (applied for concurrently, U.S. Plant patent appliction Ser. No. 13/987,664).

BACKGROUND OF THE INVENTION

The present invention relates to a new and distinct cultivar of *X Heucherella* and given the cultivar name of 'Copper Cascade'. *Heucherella* is in the family Saxifragaceae. *X Heucherella* 'Copper Cascade' originated from a controlled cross between *Heuchera* K521-1-1 (a proprietary unreleased *Heuchera*), as the seed parent, and *Tiarella* 42-2 (a proprietary unreleased *Tiarella*), as the pollen parent.

Compared to the seed parent *Heuchera* K521-1-1, the new cultivar is trailing with red to rust colored leaves with red to brown centers rather than clumping with pink to khaki colored leaves.

Compared to the pollen parent *Tiarella* 42-2, the new cultivar has red colored leaves rather than green.

Compared to its sibling, *X Heucherella* 'Gold Cascade', the new cultivar has red colored foliage rather than chartreuse.

Compared to *X Heucherella* 'Redstone Falls', U.S. Plant Pat. No. 22,394, the new cultivar has a finer habit and stems, and with smaller leaves with pinker tones and that are less lobed and with a stronger center pattern.

This new *X Heucherella* is uniquely characterized by:

1. red colored leaves with a pinkish veil and dark pattern along veins,
2. a low dense trailing habit with good branching,
3. medium size, ovate to orbicular leaves with shallow palmate lobing, and
4. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 6-month-old *X Heucherella* 'Copper Cascade' in a 1 gallon container in the greenhouse in spring in Canby, Oreg.

FIG. 2 shows 9-month-old plants with flowers in summer grown in part shade in the trail bed in Canby, Oreg.

DETAILED PLANT DESCRIPTION

The following is a detailed description of the new *X Heucherella* cultivar based on observations of a six month-old specimens growing in a one gallon container in a cool greenhouse in June in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart*, 5$^{th}$ edition.

Plant:

*Form.*—Basal rosette with trailing stems, herbaceous perennial.

*Hardiness.*—USDA Zone 4 to 9.

*Size.*—16 cm tall from top of the foliage to the ground and 42 cm wide before trailing down.

*Habit.*—Mounding and trailing.

*Vigor*.—Excellent.

*Roots*.—Fibrous, freely branching, fine, and white in color.

Stem:

*Size*.—3 mm wide and grows to 50 cm long.

*Internode length*.—2.5 cm to 4 cm.

*Stem color*.—Greyed Purple 183C.

Leaf:

*Type*.—Simple.

*Arrangement*.—Rosette and alternate.

*Shape*.—Broadly ovate.

*Lobing/division*.—5 to 7 shallow palmate lobes.

*Venation*.—Palmate.

*Margins*.—Crenate and slightly undulate.

*Apex*.—Mucronulate.

*Base*.—Cordate, usually overlapping.

*Blade size*.—Basal leaves grow to 10.5 cm long and 10 cm wide, stem leaves grow to 8.5 cm long and 8 cm wide.

*Surface texture*.—Glandular both surfaces.

*Petiole description*.—On basal leaf grows to 15 cm long and 1.5 mm wide, on stem grows to 7 cm long and 1.5 mm wide, both with glandular hairs and Greyed Purple 183C.

*Leaf color*.—Topside new and mature leaves Orange Red N34A covered in a veil of Red 36D all over except on margins and veins Orange Red 35D and with a dark blotch close to veins Greyed Purple 187A, bottom side between Red Purple 59A and Greyed Purple 186A; topside older leaves Greyed Orange 177A covered with a veil of White NN155A to White 156D except margins and veins Orange Red 35D and with a dark blotch Greyed Purple 187A, bottom side between Red Purple 59A and Greyed Purple 186A.

Inflorescence:

*Size*.—Usually 15 cm long and 3 mm wide.

*Type*.—Raceme.

*Number of flowers per raceme*.—About 50.

*Number of racemes*.—About 5.

*Peduncle*.—Grows to 16 cm long, 1.5 mm wide at base, 0 to 2 petiolate floral leaves (blades grow to 3 cm long and 2.8 cm wide, ovate, shallowly 3 to 5 lobed, tip mucronulate, margin incised, base truncate, glandular hairs on both sides, Orange Red N34A covered in a veil of Red 36D all over except on margins and veins), glandular hairs, Greyed Red 183A.

*Pedicel*.—Grows to 7 mm long, with glandular hairs, Greyed Orange 177D.

*Bloom period*.—May to July in Canby, Oreg.

Flower bud:

*Size*.—4 mm long and 2 mm wide.

*Description*.—Glandular puberulent, ovoid.

*Color*.—White NN155A.

Flower:

*Type*.—Imperfect.

*Shape*.—Campanulate.

*Size*.—6 mm deep and 6 mm wide.

*Petal description*.—5 in number, stellate, linear to spatulate, 3 mm to 4 mm long and 0.5 mm wide, reflexed slightly, tip acuminate, base attenuate, margin entire, glabrous and White NN155B on both sides.

*Calyx description*.—5 mm deep and 3 mm wide, campanulate, with 5 lobes, divided 1/2 way to the base, 3 mm long and 1 mm wide, oblong, glandular hairs on back sides, glabrous inside, tip obtuse, margin entire, White NN155B on both sides.

*Stamen description*.—None.

*Pistil description*.—10 in number, grow to 4 mm long and 1.5 mm wide, ovaries grow to 3 mm long and 1.5 wide, Yellow Green 145B, beaked style 2 mm long White NN155B.

*Fragrance*.—None.

*Lastingness*.—Each raceme blooms for about 2 weeks on the plant.

*Flower attitude*.—Semi-outwards.

*Flowering stem attitude*.—Upright.

Fruit and seed: None.

Disease and pest tolerance: The new cultivar is typical to the genus. No known resistances to pests or diseases. No problems have been found in Canby, Oreg.

I claim:

1. A new and distinct *X Heucherella* plant as herein illustrated and described.

* * * * *

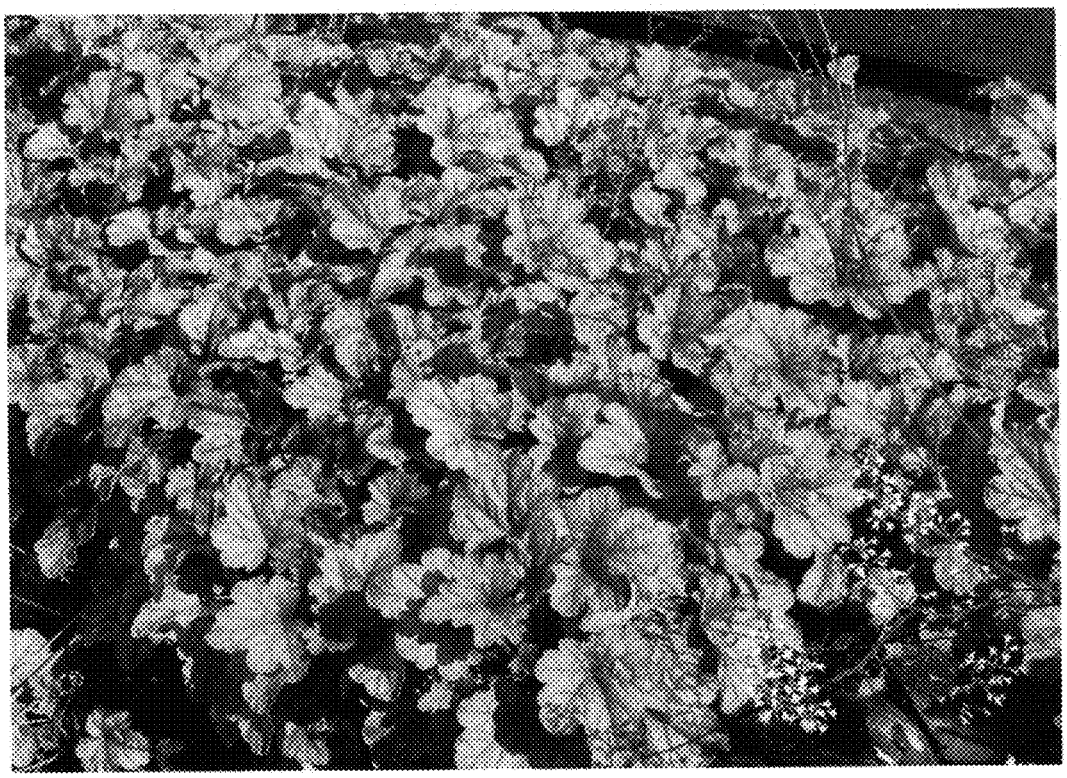

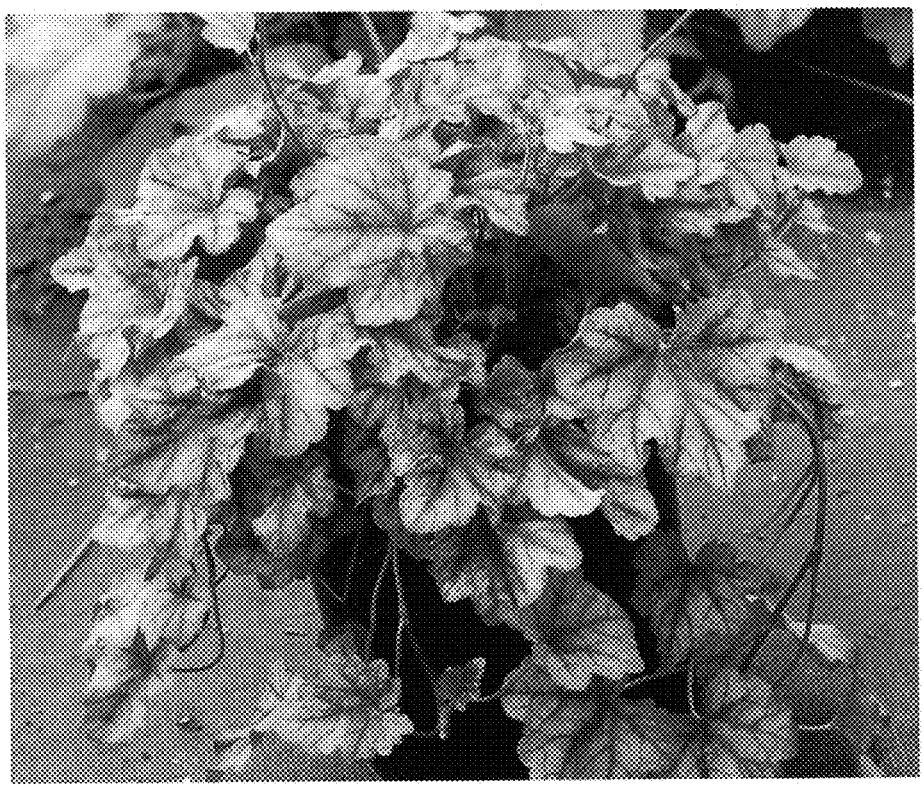
FIG. 1 above, FIG. 2 below